(12) United States Patent
Möckel et al.

(10) Patent No.: US 6,830,921 B2
(45) Date of Patent: Dec. 14, 2004

(54) NUCLEOTIDE SEQUENCES WHICH CODE FOR THE ACP GENE

(75) Inventors: Bettina Möckel, Düsseldorf (DE); Anke Weissenborn, Tübingen (DE); Walter Pfefferle, Halle (DE); Hermann Sahm, Jülich (DE); Lothar Eggeling, Jülich (DE); Madhavan Nampoothiri, Kerala (IN)

(73) Assignee: Degussa AG, Dusseldorf (DE)

( * ) Notice: Subject to any disclaimer, the term of this patent is extended or adjusted under 35 U.S.C. 154(b) by 144 days.

(21) Appl. No.: 09/852,137

(22) Filed: May 10, 2001

(65) Prior Publication Data

US 2002/0055154 A1 May 9, 2002

(30) Foreign Application Priority Data

May 12, 2000 (DE) ........................................ 100 23 400

(51) Int. Cl.$^7$ ................................................. C12N 1/20
(52) U.S. Cl. .............................. 435/252.32; 435/252.1; 435/252.32; 435/320.1; 530/300; 536/23.1
(58) Field of Search .......................... 435/252.1, 252.3, 435/252.32, 203.1; 530/300; 536/23.1

(56) References Cited

FOREIGN PATENT DOCUMENTS

| EP | 0435132 | 7/1991 |
|---|---|---|
| EP | 1 108 790 A2 | 6/2001 |
| EP | 1 108 790 | 6/2001 |
| WO | 01/00805 | 1/2001 |
| WO | WO 01/83759 | 11/2001 |

OTHER PUBLICATIONS

Leaver. Accession X63761. May 26, 1993 (Alignment No. 1).*
Attwood et al. Which craft is best in bioinformatics? Comput. Chem. 2001, vol. 25(4), pp. 329–339.*
Ponting, C.P. Issues in predicting protein function from sequence. Brief. Bioinform. Mar. 2001, vol. 2(1), pp. 19–29.*
Ehmann et al., "Lysine biosynthesis in Saccharomyces cerevisiae: Mechanism of alpha–aminoadipate reductase (Lys2) involves posttranslational phosphopantetheinylation by Lys5", Biochemistry, vol. 38, No. 19, 1999, pp. 6171–6177.
Eikmanns et al., "Identification, sequence analysis, and expression of a corynebacterium glutamicum gene cluster encoding the three glycolytic enzymes glyceraldehyde–3–phosphate dehydrogenase, 3–phosphoglycerate kinase, and triosephosphate isomerase", Journal of Bacteriology, vol. 174, No. 19, 1992. pg. 6076–6086.
Vrljic et al., "A new type of transporter with a new type of cellular function: L–lysine export from corynebacterium glutamicum", Molecular Microbiology, vol. 22, No. 5, 1999, pp. 815–826.
Peters–Wendisch et al., "Pyruvate carboxylase as an anaplerotic enzyme in Corynebacterium glutamicum", Microbiology vol. 143, no. part 4, 1997, pp. 1095–1103.
Database EMBL Accession No. AL023635.
Database TREMBL Database Accession No. 069475.
Database Biosis Database Accession No. PREV199089013841.
Database EMBL; Accession No. AL022374; XP002189182.
Database WPI; Accession No. XP002189183.
Kramer, "Genetic and physiological approaches for the production of amino acids", Journal of Biotechnology, vol. 45, No. 1, pp. 1–21.
Eikmanns et al., "Molecular aspects of lysine threonine, and isoleucine biosynthesis in Corynebacterium glutamicum", Antonie Van Leeuwenhoek, vol. 64, No. 2, pp. 145–163.

* cited by examiner

Primary Examiner—Ponnathapu Achutamurthy
Assistant Examiner—Christian L. Fronda
(74) Attorney, Agent, or Firm—Pillsbury Winthrop LLP (57) ABSTRACT

The invention relates to an isolated polynucleotide comprising a polynucleotide sequence chosen from the group consisting of a) polynucleotide which is identical to the extent of at least 70 % to a polynucleotide which codes for a polypeptide which comprises the amino acid sequence of SEQ ID No. 2,
b) polynucleotide which codes for a polypeptide which comprises an amino acid sequence which is identical to the extent of at least 70 % to the amino acid sequence of SEQ ID No. 2,
c) polynucleotide which is complementary to the polynucleotides of a) or b), and
d) polynucleotide comprising at least 15 successive nucleotides of the polynucleotide sequence of a), b) or c), a process for the fermentative preparation of L–amino acids with enhancement of the acp gene and the use of the polynucleotide as a primer or hybridization probe.

7 Claims, 2 Drawing Sheets

Figure 1: Plasmid pJC1acp

Figure 2: Growth of C. glutamicum ATCC 13032 (♦) and ATCC 13032/pJCacp (■).

```
                        SEQUENCE LISTING

<160> NUMBER OF SEQ ID NOS: 4

<210> SEQ ID NO 1
<211> LENGTH: 551
<212> TYPE: DNA
<213> ORGANISM: Corynebacterium glutamicum
<220> FEATURE:
<221> NAME/KEY: CDS
<222> LOCATION: (58)..(348)
<221> NAME/KEY: RBS
<222> LOCATION: (41)..(49)

<400> SEQUENCE: 1
gccgcgttgt gtatccataa gtcttagcct acaagcgctt tgaggtagtt tgggatc         57 atg gat ttc aac gac aaa gcc gct tca gaa aac gct gta aag act ggc     105
Met Asp Phe Asn Asp Lys Ala Ala Ser Glu Asn Ala Val Lys Thr Gly
 1               5                  10                  15 gca gaa ggc ccc aac gtt ttc gcg agc gtg gcc aag att ttg cag gat     153
Ala Glu Gly Pro Asn Val Phe Ala Ser Val Ala Lys Ile Leu Gln Asp
             20                  25                  30 gtt ggc gga att tca gcc gaa gac gtc act ccg gaa tct cgt ttt act     201
Val Gly Gly Ile Ser Ala Glu Asp Val Thr Pro Glu Ser Arg Phe Thr
         35                  40                  45 gag gat ttg gca gtg agc tca ctc aat tac atc gag ttg att gtc aat     249
Glu Asp Leu Ala Val Ser Ser Leu Asn Tyr Ile Glu Leu Ile Val Asn
     50                  55                  60 gcg gag gac gca ttt ggt gtt cgc att gag gac gcc gat gcc aag gat     297
Ala Glu Asp Ala Phe Gly Val Arg Ile Glu Asp Ala Asp Ala Lys Asp
 65                  70                  75                  80 ttg acc acc gtg cag gat ttg att gac ttt att aac acc aat aag gct     345
Leu Thr Thr Val Gln Asp Leu Ile Asp Phe Ile Asn Thr Asn Lys Ala
                 85                  90                  95 gat tagcgggaaa atttcgccca aaacagggac aatggtgtta tgacagtgaa           398
Asp catttcatat ctgaccgaca tggacggcgt cctcatcaaa gagggcgaga taattccggg     458
```

```
                                                              -continued tgcagatcgt tttcttcagt ctctcaccga taacaatgtg gagtttatgg ttttgaccaa        518
caactccatt ttcaccccga gggatctttc tgc                                    551

<210> SEQ ID NO 2
<211> LENGTH: 97
<212> TYPE: PRT
<213> ORGANISM: Corynebacterium glutamicum

<400> SEQUENCE: 2

Met Asp Phe Asn Asp Lys Ala Ala Ser Glu Asn Ala Val Lys Thr Gly
  1               5                  10                  15

Ala Glu Gly Pro Asn Val Phe Ala Ser Val Ala Lys Ile Leu Gln Asp
             20                  25                  30

Val Gly Gly Ile Ser Ala Glu Asp Val Thr Pro Glu Ser Arg Phe Thr
         35                  40                  45

Glu Asp Leu Ala Val Ser Ser Leu Asn Tyr Ile Glu Leu Ile Val Asn
     50                  55                  60

Ala Glu Asp Ala Phe Gly Val Arg Ile Glu Asp Ala Asp Ala Lys Asp
 65                  70                  75                  80

Leu Thr Thr Val Gln Asp Leu Ile Asp Phe Ile Asn Thr Asn Lys Ala
                 85                  90                  95

Asp

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 3
tcggggtgaa aatggagttg t                                                  21

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 4
aagcgctttg aggtagtttg                                                    20
```

NUCLEOTIDE SEQUENCES WHICH CODE FOR THE ACP GENE

CROSS REFERENCE TO RELATED APPLICATIONS the present application claims priority under 35 U.S.C. §to German application 100 23 400.3, filed May 12, 2000.

FIELD OF THE INVENTION

The invention provides nucleotide sequences which code for the acp gene and a process for the fermentative preparation of amino acids, in particular L-lysine, using coryneform bacteria in which the acp gene is enhanced. The acp gene codes for the acyl carrier protein.

PRIOR ART

Amino acids, in particular L-lysine, are used in human medicine and in the pharmaceuticals industry, but in particular in animal nutrition.

It is known that amino acids are prepared by fermentation from strains of coryneform bacteria, in particular *Corynebacterium glutamicum*. Because of their great importance, work is constantly being undertaken to improve the preparation processes. Improvements to the processes can relate to fermentation measures, such as e. g. stirring and supply of oxygen, or the composition of the nutrient media, such as e. g. the sugar concentration during the fermentation, or the working up to the product form by e. g. ion exchange chromatography, or the intrinsic output properties of the microorganism itself.

Methods of mutagenesis, selection and mutant selection are used to improve the output properties of these microorganisms. Strains which are resistant to antimetabolites, such as e. g. the lysine analogue S-(2-aminoethyl)-cysteine, or are auxotrophic for metabolites of regulatory importance and produce L-amino acids, such as e. g. L-lysine, are obtained in this manner.

Methods of the recombinant DNA technique have also been employed for some years for improving the strain of Corynebacterium strains which produce amino acids, by amplifying individual amino acid biosynthesis genes and investigating the effect on the amino acid production. Review articles in this context are to be found, inter alia, in Kinoshita ("Glutamic Acid Bacteria", in: Biology of Industrial Microorganisms, Demain and Solomon (Eds.), Benjamin Cummings, London, UK, 1985, 115–142), Hilliger (BioTec 2, 40–44 (1991)), Eggeling (Amino Acids 6:261–272 (1994)), Jetten and Sinskey (Critical Reviews in Biotechnology 15, 73–103 (1995)) and Sahm et al. (Annuals of the New York Academy of Science 782, 25–39 (1996)).

OBJECT OF THE INVENTION

The inventors had the object of providing new measures for improved fermentative preparation of amino acids, in particular L-lysine.

DESCRIPTION OF THE INVENTION

Amino acids, in particular L-lysine, are used in human medicine, in the pharmaceuticals industry and in particular in animal nutrition. There is therefore a general interest in providing new improved processes for the preparation of amino acids, in particular L-lysine.

When L-lysine or lysine is mentioned in the following, not only the base but also the salts, such as e. g. lysine monohydrochloride or lysine sulfate, are also meant by this.

The invention provides an isolated polynucleotide from coryneform bacteria, comprising a polynucleotide sequence chosen from the group consisting of a) polynucleotide which is identical to the extent of at least 70% to a polynucleotide which codes for a polypeptide which comprises the amino acid sequence of SEQ ID No. 2, b) polynucleotide which codes for a polypeptide which comprises an amino acid sequence which is identical to the extent of at least 70% to the amino acid sequence of SEQ ID No. 2, c) polynucleotide which is complementary to the polynucleotides of a) or b), and d) polynucleotide comprising at least 15 successive nucleotides of the polynucleotide sequence of a), b) or c).

The invention also provides the polynucleotide according to claim 1, this preferably being a DNA which is capable of replication, comprising:

(i) the nucleotide sequence shown in SEQ ID No. 1, or (ii) at least one sequence which corresponds to sequence (i) within the range of the degeneration of the genetic code, or (iii) at least one sequence which hybridizes with the sequence complementary to sequence (i) or (ii), and optionally (iv) sense mutations of neutral function in (i).

THE INVENTION ALSO PROVIDES a polynucleotide according to claim 4, comprising the nucleotide sequence as shown in SEQ ID no. 1, a polynucleotide according to claim 6, which codes for a polypeptide which comprises the amino acid sequence as shown in SEQ ID No. 2, a vector containing the DNA sequence of *C. glutamicum* which codes for the acp gene, contained in the vector pJC1acp, deposited in *Corynebacterium glutamicum* under number DSM 13247, and coryneform bacteria serving as the host cell, which contain the vector or in which the acp gene is enhanced.

The invention also provides polynucleotides which substantially comprise a polynucleotide sequence, which are obtainable by screening by means of hybridization of a corresponding gene library, which comprises the complete gene with the polynucleotide sequence corresponding to SEQ ID No. 1, with a probe which comprises the sequence of the polynucleotide mentioned, according to SEQ ID no. 1 or a fragment thereof, and isolation of the DNA sequence mentioned.

Polynucleotide sequences according to the invention are suitable as hybridization probes for RNA, cDNA and DNA, in order to isolate, in the full length, cDNA which code for the acyl carrier protein and to isolate those cDNA or genes which have a high similarity with the sequence of the acyl carrier protein gene.

Polynucleotide sequences according to the invention are furthermore suitable as primers for the preparation of DNA of genes which code for acyl carrier proteins by the polymerase chain reaction (PCR).

Such oligonucleotides which serve as probes or primers comprise at least 30, preferably at least 20, very particularly preferably at least 15 successive nucleotides. Oligonucleotides which have a length of at least 40 or 50 nucleotides are also suitable.

"Isolated" means separated out of its natural environment.

"Polynucleotide" in general relates to polyribonucleotides and polydeoxyribonucleotides, it being possible for these to be non-modified RNA or DNA or modified RNA or DNA.

"Polypeptides" are understood as meaning peptides or proteins which comprise two or more amino acids bonded via peptide bonds.

The polypeptides according to the invention include a polypeptide according to SEQ ID No. 2, in particular those with the biological activity of the acyl carrier protein and also those which are at least 70% identical to the polypeptide according to SEQ ID No. 2, and preferably are identical to the extent of at least 80% and in particular to the extent of at least 90% to 95% to the polypeptide according to SEQ ID no. 2 and have the activity mentioned.

The invention furthermore provides a process for the fermentative preparation of amino acids, in particular L-lysine, using coryneform bacteria which in particular already produce an amino acid, and in which the nucleotide sequences which code for the acp gene are enhanced, in particular over-expressed.

The term "enhancement" in this connection describes the increase in the intracellular activity of one or more enzymes in a microorganism which are coded by the corresponding DNA, for example by increasing the number of copies of the gene or genes, using a potent promoter or using a gene which codes for a corresponding enzyme having a high activity, and optionally combining these measures.

The microorganisms which the present invention provides can prepare L-amino acids, in particular L-lysine, from glucose, sucrose, lactose, fructose, maltose, molasses, starch, cellulose or from glycerol and ethanol. They can be representatives of coryneform bacteria, in particular of the genus Corynebacterium. Of the genus Corynebacterium, there may be mentioned in particular the species *Corynebacterium glutamicum*, which is known among experts for its ability to produce L-amino acids.

Suitable strains of the genus Corynebacterium, in particular of the species *Corynebacterium glutamicum*, are, for example, the known wild-type strains
*Corynebacterium glutamicum* ATCC13032
*Corynebacterium acetoglutamicum* ATCC15806
*Corynebacterium acetoacidophilum* ATCC13870
*Corynebacterium thermoaninogenes* FERM BP-1539
*Corynebacterium melassecola* ATCC17965
*Brevibacterium flavum* ATCC14067
*Brevibacterium lactofermentum* ATCC13869 and
*Brevibacterium divaricatum* ATCC14020
and L-lysine-producing mutants or strains prepared therefrom, such as, for example
*Corynebacterium glutamicum* FERM-P 1709
*Brevibacterium flavum* FERM-P 1708
*Brevibacterium lactofermentum* FERM-P 1712
*Corynebacterium glutamicum* FERM-P 6463
*Corynebacterium glutamicum* FERM-P 6464 and
*Corynebacterium glutamicum* DSM5715.

The inventors have succeeded in isolating the new acp gene of *C. glutamicum* which codes for the acyl carrier protein.

To isolate the acp gene or also other genes of *C. glutamicum*, a gene library of this microorganism is first set up in *E. coli*. The setting up of gene libraries is described in generally known textbooks and handbooks. The textbook by Winnacker: Gene und Klone, Eine Einführung in die Gentechnologie [Genes and Clones, An Introduction to Genetic Engineering] (Verlag Chemie, Weinheim, Germany, 1990) or the handbook by Sambrook et al.: Molecular Cloning, A Laboratory Manual (Cold Spring Harbor Laboratory Press, 1989) may be mentioned as an example. A very well-known gene library is that of the *E. coli* K-12 strain W3110 set up in λ vectors by Kohara et al. (Cell 50, 495–508 (1987)).

Bathe et al. (Molecular and General Genetics, 252:255–265, 1996) describe a gene library of *C. glutamicum* ATCC13032, which was set up with the aid of the cosmid vector SuperCos I (Wahl et al., 1987, Proceedings of the National Academy of Sciences USA, 84:2160–2164) in the *E. coli* K-12 strain NM554 (Raleigh et al., 1988, Nucleic Acids Research 16:1563–1575). Börmann et al. (Molecular Microbiology 6(3), 317–326 (1992)) in turn describe a gene library of *C. glutamicum* ATCC13032 using the cosmid pHC79 (Hohn and Collins, Gene 11, 291–298 (1980)). To prepare a gene library of *C. glutamicum* in *E. coli* it is also possible to use plasmids such as pBR322 (Bolivar, Life Sciences, 25, 807–818 (1979)) or pUC9 (Vieira et al., 1982, Gene, 19:259–268). Suitable hosts are, in particular, those *E. coli* strains which are restriction- and recombination-defective. An example of these is the strain DH5αmcr, which has been described by Grant et al. (Proceedings of the National Academy of Sciences USA, 87 (1990) 4645–4649). The long DNA fragments cloned with the aid of cosmids can then in turn be subcloned and subsequently sequenced in the usual vectors which are suitable for sequencing, such as is described e. g. by Sanger et al. (Proceedings of the National Academy of Sciences of the United States of America, 74:5463–5467, 1977).

The new DNA sequence of *C. glutamicum* which codes for the acp gene and which, as SEQ ID No. 1, is a constituent of the present invention has been obtained in this manner. The amino acid sequence of the corresponding protein has furthermore been derived from the present DNA sequence by the methods described above. The resulting amino acid sequence of the acp gene product is shown in SEQ ID No. 2.

Coding DNA sequences which result from SEQ ID No. 1 by the degeneracy of the genetic code are also a constituent of the invention. In the same way, DNA sequences which hybridize with SEQ ID No. 1 or parts of SEQ ID No. 1 are a constituent of the invention. Conservative amino acid exchanges, such as e. g. exchange of glycine for alanine or of aspartic acid for glutamic acid in proteins, are furthermore known among experts as "sense mutations" which do not lead to a fundamental change in the activity of the protein, i.e. are of neutral function. It is furthermore known that changes on the N and/or C terminus of a protein cannot substantially impair or can even stabilize the function thereof. Information in this context can be found by the expert, inter alia, in Ben-Bassat et al. (Journal of Bacteriology 169:751–757 (1987)), in O'Regan et al. (Gene 77:237–251 (1989)), in Sahin-Toth et al. (Protein Sciences 3:240–247 (1994)), in Hochuli et al. (Bio/Technology 6:1321–1325 (1988)) and in known textbooks of genetics and molecular biology. Amino acid sequences which result in a corresponding manner from SEQ ID No. 2 are also a constituent of the invention.

In the same way, DNA sequences which hybridize with SEQ ID No. 1 or parts of SEQ ID No. 1 are a constituent of the invention. Finally, DNA sequences which are prepared by the polymerase chain reaction (PCR) using primers which result from SEQ ID NO. 1 are a constituent of the invention. Such oligonucleotides typically have a length of at least 15 nucleotides.

Instructions for identifying DNA sequences by means of hybridization can be found by the expert, inter alia, in the handbook "The DIG System Users Guide for Filter Hybridization" from Roche Diagnostics GmbH (Mannheim, Germany, 1993) and in Liebl et al. (International Journal of Systematic Bacteriology (1991) 41: 255–260). Instructions for amplification of DNA sequences with the aid of the polymerase chain reaction (PCR) can be found by the expert, inter alia, in the handbook by Gait: Oligonucleotide synthesis: a practical approach (IRL Press, Oxford, UK, 1984) and in Newton and Graham: PCR (Spektrum Akademischer Verlag, Heidelberg, Germany, 1994).

The inventors have found that coryneform bacteria produce amino acids, in particular L-lysine, in an improved manner after enhancement of the acp gene.

To achieve an enhancement, in particular an over-expression, the number of copies of the corresponding genes can be increased, or the promoter and regulation region or the ribosome binding site upstream of the structural gene can be mutated. Expression cassettes which are incorporated upstream of the structural gene act in the same way. By inducible promoters, it is additionally possible to increase the expression in the course of fermentative L-lysine production. The expression is likewise improved by measures to prolong the life of the m-RNA. Furthermore, the enzyme activity is also increased by preventing the degradation of the enzyme protein. The genes or gene constructs can either be present in plasmids with a varying number of copies, or can be integrated and amplified in the chromosome. Alternatively, an over-expression of the genes in question can furthermore be achieved by changing the composition of the media and the culture procedure.

Instructions in this context can be found by the expert, inter alia, in Martin et al. (Bio/Technology 5, 137–146 (1987)), in Guerrero et al. (Gene 138, 35–41 (1994)), Tsuchiya and Morinaga (Bio/Technology 6, 428–430 (1988)), in Eikmanns et al. (Gene 102, 93–98 (1991)), in European Patent Specification EPS 0 472 869, in U.S. Pat. No. 4,601,893, in Schwarzer and Puhler (Bio/Technology 9, 84–87 (1991)), in Reinscheid et al. (Applied and Environmental Microbiology 60, 126–132 (1994)), in LaBarre et al. (Journal of Bacteriology 175, 1001–1007 (1993)), in Patent Application WO 96/15246, in Malumbres et al. (Gene 134, 15–24 (1993)), in Japanese Laid-Open Specification JP-A-10-229891, in Jensen and Hammer (Biotechnology and Bioengineering 58, 191–195 (1998)), in Makrides (Microbiological Reviews 60:512–538 (1996)) and in known textbooks of genetics and molecular biology.

By way of example, the acp gene according to the invention was over-expressed with the aid of plasmids.

Suitable plasmids are those which are replicated in coryneform bacteria. Numerous known plasmid vectors, such as e. g. pZ1 (Menkel et al., Applied and Environmental Microbiology (1989) 64: 549–554), pEKEx1 (Eikmanns et al., Gene 102:93–98 (1991)) or pHS2-1 (Sonnen et al., Gene 107:69–74 (1991)) are based on the cryptic plasmids pHM1519, pBL1 or pGA1. Other plasmid vectors, such as e. g. those based on pCG4 (U.S. Pat. No. 4,489,160), or pNG2 (Serwold-Davis et al., FEMS Microbiology Letters 66, 119–124 (1990)), or pAG1 (U.S. Pat. No. 5,158,891), can be used in the same manner.

An example of a plasmid, with the aid of which the acp gene can be over-expressed is pJC1acp (FIG. 1), which is based on the E. coli-C. glutamicum shuttle vector pJC1 (Cremer et al., 1990, Molecular and General Genetics 220: 478–480) and contains the DNA sequence of C. glutamicum which codes for the acp gene. It is contained in the strain DSM5715/pJC1acp.

Plasmid vectors which are furthermore suitable are those with the aid of which the process of gene amplification by integration into the chromosome can be used, as has been described, for example, by Reinscheid et al. (Applied and Environmental Microbiology 60, 126–132 (1994)) for duplication or amplification of the hom-thrB operon. In this method, the complete gene is cloned in a plasmid vector which can replicate in a host (typically E. coli), but not in C. glutamicum. Possible vectors are, for example, pSUP301 (Simon et al., Bio/Technology 1, 784–791 (1983)), pK18mob or pK19mob (Schäfer et al., Gene 145, 69–73 (1994)), pGEM-T (Promega corporation, Madison, Wis., USA), pCR2.1-TOPO (Shuman (1994). Journal of Biological Chemistry 269:32678-84; U.S. Pat. No. 5,487,993), pCR®Blunt (Invitrogen, Groningen, The Netherlands; Bernard et al., Journal of Molecular Biology, 234: 534–541 (1993)) or pEM1 (Schrumpf et al, 1991, Journal of Bacteriology 173:4510–4516). The plasmid vector which contains the gene to be amplified is then transferred into the desired strain of C. glutamicum by conjugation or transformation. The method of conjugation is described, for example, by Sch äfer et al. (Applied and Environmental Microbiology 60, 756–759 (1994)). Methods for transformation are described, for example, by Thierbach et al. (Applied Microbiology and Biotechnology 29, 356–362 (1988)), Dunican and Shivnan (Bio/Technology 7, 1067–1070 (1989)) and Tauch et al. (FEMS Microbiological Letters 123, 343–347 (1994)). After homologous recombination by means of a "cross over" event, the resulting strain contains at least two copies of the gene in question.

In addition, it may be advantageous for the production of amino acids, in particular L-lysine, to enhance or over-express one or more enzymes of the particular biosynthesis pathway, of glycolysis, of anaplerosis or of amino acid export, in addition to the acp gene.

Thus, for example, for the preparation of L-lysine, at the same time one or more of the genes chosen from the group consisting of the dapA gene which codes for dihydrodipicolinate synthase (EP-B 0 197 335), or at the same time the mqo gene which codes for malate-quinone oxidoreductase (Molenaar et al., European Journal of Biochemistry 254, 395–403 (1998)), or the dapE gene which codes for succinyl diaminopimelate desuccinylase (Accession No. Q59284).

the gap gene which codes for glyceraldehyde 3-phosphate dehydrogenase (Eikmanns (1992), Journal of Bacteriology 174:6076–6086), or the tpi gene which codes for triose phosphate isomerase (Eikmanns (1992), Journal of Bacteriology 174:6076–6086), or the lysC gene which codes for a feed-back resistant aspartate kinase (Accession No. P26512)

the pgk gene which codes for 3-phosphoglycerate kinase (Eikmanns (1992), Journal of Bacteriology 174:6076–6086), or the pyc gene which codes for pyruvate carboxylase (Eikmanns (1992), Journal of Bacteriology 174:6076–6086), or the lysE gene which codes for lysine export (DE-A-195 48 222)

can be enhanced, in particular over-expressed or amplified, at the same time.

It may furthermore be advantageous for the production of amino acids, in particular L-lysine, in addition to the enhancement of the acp gene, at the same time for the pck gene which codes for phosphoenol pyruvate carboxykinase (DE 199 50 409.1 DSM 13047) and/or the pgi gene which codes for glucose 6-phosphate isomerase (U.S. Pat. No. 09/396,478, DSM 12969) and/or the poxB gene which codes for pyruvate oxidase (DE:1995 1975.7)
to be attenuated.

In addition to over-expression of the acp gene it may furthermore be advantageous, for the production of amino acids, in particular L-lysine, to eliminate undesirable side reactions, (Nakayama: "Breeding of Amino Acid Producing Micro-organisms", in: Overproduction of Microbial Products, Krumphanzl, Sikyta, Vanek (eds.), Academic Press, London, UK, 1982).

The microorganisms prepared according to the invention can be cultured continuously or discontinuously in the batch process (batch culture) or in the fed batch (feed process) or repeated fed batch process (repetitive feed process) for the purpose of production of amino acids, in particular L-lysine. A summary of known culture methods is described in the textbook by Chmiel (Bioprozesstechnik 1. Einführung in die Bioverfahrenstechnik [Bioprocess Technology 1. Introduction to Bioprocess Technology (Gustav Fischer Verlag, Stuttgart, 1991)) or in the textbook by Storhas (Bioreaktoren und periphere Einrichtungen [Bioreactors and Peripheral Equipment] (Vieweg Verlag, Braunschweig/Wiesbaden, 1994)).

The culture medium to be used must meet the requirements of the particular strains in a suitable manner. Descriptions of culture media for various microorganisms are contained in the handbook "Manual of Methods for General Bacteriology" of the American Society for Bacteriology (Washington D.C., USA, 1981). Sugars and carbohydrates, such as e. g. glucose, sucrose, lactose, fructose, maltose, molasses, starch and cellulose, oils and fats, such as e. g. soya oil, sunflower oil, groundnut oil and coconut fat, fatty acids, such as e. g. palmitic acid, stearic acid and linoleic acid, alcohols, such as e. g. glycerol and ethanol, and organic acids, such as e. g. acetic acid, can be used as the source of carbon. These substance can be used individually or as a mixture. Organic nitrogen-containing compounds, such as peptones, yeast extract, meat extract, malt extract, corn steep liquor, soya bean flour and urea, or inorganic compounds, such as ammonium sulfate, ammonium chloride, ammonium phosphate, ammonium carbonate and ammonium nitrate, can be used as the source of nitrogen. The sources of nitrogen can be used individually or as a mixture. Phosphoric acid, potassium dihydrogen phosphate or dipotassium hydrogen phosphate or the corresponding sodium-containing salts can be used as the source of phosphorus. The culture medium must furthermore comprise salts of metals, such as e. g. magnesium sulfate or iron sulfate, which are necessary for growth. Finally, essential growth substances, such as amino acids and vitamins, can be employed in addition to the abovementioned substances. Suitable precursors can moreover be added to the culture medium. The starting substances mentioned can be added to the culture in the form of a single batch, or can be fed in during the culture in a suitable manner.

Basic compounds, such as sodium hydroxide, potassium hydroxide, ammonia or aqueous ammonia, or acid compounds, such as phosphoric acid or sulfuric acid, can be employed in a suitable manner to control the pH of the culture. Antifoams, such as e. g. fatty acid polyglycol esters, can be employed to control the development of foam. Suitable substances having a selective action, such as e. g. antibiotics, can be added to the medium to maintain the stability of plasmids. To maintain aerobic conditions, oxygen or oxygen-containing gas mixtures, such as e. g. air, are introduced into the culture. The temperature of the culture is usually 20° C. to 45° C., and preferably 25° C. to 40° C. Culturing is continued until a maximum of lysine has formed. This target is usually reached within 10 hours to 160 hours.

The analysis of L-lysine can be carried out by anion exchange chromatography with subsequent ninhydrin derivatization, as described by Spackman et al. (Analytical Chemistry, 30, (1958), 1190).

The following microorganism has been deposited at the Deutsche Sammlung für Mikroorganismen und Zellkulturen (DSMZ=German Collection of Microorganisms and Cell Cultures, Braunschweig, Germany) in accordance with the Budapest Treaty:

Corynebacterium glutamicum strain DSM5715/pJC1acp as DSM 13247

The process according to the invention is used for the fermentative preparation of amino acids, in particular L-lysine

EXAMPLES

The present invention is explained in more detail in the following with the aid of embodiment examples.

Example 1

Preparation of a Genomic Cosmid Gene Library From Corynebacterium glutamicum ATCC 13032

Chromosomal DNA from Corynebacterium glutamicum ATCC 13032 was isolated as described by Tauch et al. (1995, Plasmid 33:168–179) and partly cleaved with the restriction enzyme Sau3AI (Amersham Pharmacia, Freiburg, Germany, Product Description Sau3AI, Code No. 27-0913-02). The DNA fragments were dephosphorylated with shrimp alkaline phosphatase (Roche Diagnostics GmbH, Mannheim, Germany, Product Description SAP, Code No. 1758250). The DNA of the cosmid vector Super-Cos1 (Wahl et al. (1987) Proceedings of the National Academy of Sciences USA 84:2160–2164), obtained from Stratagene (La Jolla, USA, Product Description SuperCos1 Cosmid Vector Kit, Code No. 251301) was cleaved with the restriction enzyme XbaI (Amersham Pharmacia, Freiburg, Germany, Product Description XbaI, Code No. 27-0948-02) and likewise dephosphorylated with shrimp alkaline phosphatase. The cosmid DNA was then cleaved with the restriction enzyme BamHI (Amersham Pharmacia, Freiburg, Germany, Product Description BamHI, Code No. 27-0868-04). The cosmid DNA treated in this manner was mixed with the treated ATCC 13032 DNA and the batch was treated with T4 DNA ligase (Amersham Pharmacia, Freiburg, Germany, Product Description T4-DNA-Ligase, Code No. 27-0870-04). The ligation mixture was then packed in phages with the aid of Gigapack II XL Packing Extract (Stratagene, La Jolla, USA, Product Description Gigapack II XL Packing Extract, Code No. 200217). For infection of the E. coli strain NM554 (Raleigh et al. 1988, Nucleic Acid Research 16:1563–1575) the cells were taken up in 10 mM $MgSO_4$ and mixed with an aliquot of the phage suspension. The infection and titering of the cosmid library were carried out as described by Sambrook et al. (1989, Molecular Cloning: A Laboratory Manual, Cold Spring Harbor), the cells being plated out on LB agar (Lennox, 1955, Virology, 1:190) with 100 mg/l ampicillin. After incubation overnight at 37° C., recombinant individual clones were selected.

Example 2

Isolation and Sequencing of the acp Gene

The cosmid DNA of an individual colony was isolated with the Qiaprep Spin Miniprep Kit (Product No. 27106, Qiagen, Hilden, Germany) in accordance with the manufacturer's instructions and partly cleaved with the restriction enzyme Sau3AI (Amersham Pharmacia, Freiburg, Germany, Product Description Sau3AI, Product No. 27-0913-02). The DNA fragments were dephosphorylated with shrimp alkaline phosphatase (Roche Diagnostics GmbH, Mannheim, Germany, Product Description SAP, Product No. 1758250). After separation by gel electrophoresis, the cosmid fragments in the size range of 1500 to 2000 bp were isolated with the QiaExII Gel Extraction Kit (Product No. 20021, Qiagen, Hilden, Germany). The DNA of the sequencing vector pZero-1, obtained from Invitrogen (Groningen, The Netherlands, Product Description Zero Background Cloning Kit, Product No. K2500-01) was cleaved with the restriction enzyme BamHI (Amersham Pharmacia, Freiburg, Germany, Product Description BamHI, Product No. 27-0868-04). The ligation of the cosmid fragments in the sequencing vector pZero-1 was carried out as described by Sambrook et al. (1989, Molecular Cloning: A laboratory Manual, Cold Spring Harbor), the DNA mixture being incubated overnight with T4 ligase (Pharmacia Biotech, Freiburg, Germany). This ligation mixture was then electroporated (Tauch et al. 1994, FEMS Microbiol Letters, 123:343-7) into the *E. coli* strain DH5αMCR (Grant, 1990, Proceedings of the National Academy of Sciences U.S.A., 87:4645–4649) and plated out on LB agar (Lennox, 1955, Virology, 1:190) with 50 mg/l zeocin. The plasmid preparation of the recombinant clones was carried out with Biorobot 9600 (Product No. 900200, Qiagen, Hilden, Germany). The sequencing was carried out by the dideoxy chain termination method of Sanger et al. (1977, Proceedings of the National Academy of Sciences U.S.A., 74:5463–5467) with modifications according to Zimmermann et al. (1990, Nucleic Acids Research, 18:1067). The "RR dRhodamin Terminator Cycle Sequencing Kit" from PE Applied Biosystems (Product No. 403044, Weiterstadt, Germany) was used. The separation by gel electrophoresis and analysis of the sequencing reaction were carried out in a "Rotiphoresis NF Acrylamide/Bisacrylamide" Gel (29:1) (Product No. A124.1, Roth, Karlsruhe, Germany) with the "ABI Prism 377" sequencer from PE Applied Biosystems (Weiterstadt, Germany).

The raw sequence data obtained were then processed using the Staden program package (1986, Nucleic Acids Research, 14:217–231) version 97-0. The individual sequences of the pzero1 derivatives were assembled to a continuous contig. The computer-assisted coding region analysis was prepared with the XNIP program (Staden, 1986, Nucleic Acids Research, 14:217–231). Further analyses were carried out with the "BLAST search programs" (Altschul et al., 1997, Nucleic Acids Research, 25:3389–3402), against the non-redundant databank of the "National Center for Biotechnology Information" (NCBI, Bethesda, Md., USA).

The resulting nucleotide sequence is shown in SEQ ID No. 1. Analysis of the nucleotide sequence showed an open reading frame of 291 base pairs, which was called the acp gene. The acp gene codes for a protein of 97 amino acids.

Example 3

Cloning of the acp Gene

Chromosomal DNA from *Corynebacterium glutamicum* ATCC 13032 was isolated as described by Tauch et al. (1995, Plasmid 33:168–179). A DNA fragment which carries the acp gene was amplified with the aid of the polymerase chain reaction. The following primers were used for this:

5'-TCG GGG TGA AAA TGG AGT TGT-3'  (SEQ ID NO:3)

5'-AAG CGC TTT GAG GTA GTT TG-3'  (SEQ ID NO:4)

The primers shown were synthesized by MWG Biotech (Ebersberg, Germany) and the PCR reaction was carried out by the standard PCR method of Innis et al., (PCR protocol. A guide to methods and applications, 1990, Academic Press). The primers allow amplification of a DNA fragment 510 bp in size, which carries the acp gene from *Corynebacterium glutamicum*.

After separation by gel electrophoresis, the PCR fragment was isolated from the agarose gel with the QiaExII Gel Extraction Kit (Product No. 20021, Qiagen, Hilden, Germany).

The vector pUC18 (Norrander et al., Gene (26) 101–106 (1983)) was cleaved completely with the restriction endonuclease SmaI and dephosphorylated with shrimp alkaline phosphatase (Roche Diagnostics GmbH, Mannheim, Germany, Product Description SAP, Product No. 1758250).

The PCR fragment obtained in this manner was mixed with the prepared vector pUC18 and the batch was treated with T4 DNA ligase (Amersham Pharmacia, Freiburg, Germany, Product Description T4-DNA-Ligase, Code no.27-0870-04). The ligation batch was transformed in the *E. coli* strain DH5α (Hanahan, In: DNA cloning. A practical approach. Vol. I. IRL-Press, Oxford, Washington D.C., USA). Selection of plasmid-carrying cells was made by plating out the transformation batch on LB agar (Lennox, 1955, Virology, 1:190) with 100 mg/l ampicillin. After incubation overnight at 37° C., recombinant individual clones were selected. Plasmid DNA was isolated from a transformant with the Qiaprep Spin Miniprep Kit (Product No. 27106, Qiagen, Hilden, Germany) in accordance with the manufacturer's instructions and cleaved with the restriction enzyme HindII to check the plasmid by subsequent agarose gel electrophoresis. A fragment of approx. 3600 bp is obtained. The resulting plasmid was called pUC18acp.

Example 4

Cloning of acp in the Vector pJC1

The acp gene was isolated from the plasmid pUC18acp described in example 3 by complete cleavage with the enzyme PvuII. The acp fragment 877 bp in size was isolated from the agarose gel with the QiaExII Gel Extraction Kit (Product No. 20021, Qiagen, Hilden, Germany)

The vector used was the *E. coli*-*C. glutamicum* shuttle vector pJC1 (Cremer et al., 1990, Molecular and General Genetics 220: 478–480). This plasmid was also cleaved completely with the restriction enzyme BamHI, treated with Klenow polymerase (Roche Diagnostics GmbH, Mannheim, Germany) and then dephosphorylated with shrimp alkaline phosphatase (Roche Diagnostics GmbH, Mannheim, Germany, Product Description SAP, Product No. 1758250).

The acp fragment obtained in this manner was mixed with the prepared vector pJC1 and the batch was treated with T4 DNA ligase (Amersham Pharmacia, Freiburg, Germany, Product Description T4-DNA-Ligase, Code no.27-0870-04). The ligation batch was transformed in the *E. coli* strain DH5α (Hanahan, In: DNA cloning. A practical approach. Vol. I. IRL-Press, Oxford, Washington D.C., USA). Selection of plasmid-carrying cells was made by plating out the transformation batch on LB agar (Lennox, 1955, Virology, 1:190) with 50 mg/l kanamycin. After incubation overnight at 37° C., recombinant individual clones were selected. Plasmid DNA was isolated from a transformant with the Qiaprep Spin Miniprep Kit (Product No. 27106, Qiagen, Hilden, Germany) in accordance with the manufacturer's instructions and cleaved with the restriction enzyme EcoRI to check the plasmid by subsequent agarose gel electrophoresis. The resulting plasmid was called pJC1acp.

Example 5

Transformation of the Strain DSM5715 With the Plasmid pJC1acp

The strain DSM5715 was transformed with the plasmid pJC1acp using the electroporation method described by Liebl et al., (FEMS Microbiology Letters, 53:299–303 (1989)). Selection of the transformants took place on LBHIS agar comprising 18.5 g/l brain-heart infusion broth, 0.5 M sorbitol, 5 g/l Bacto-tryptone, 2.5 g/l Bacto-yeast extract, 5 g/l NaCl and 18 g/l Bacto-agar, which had been supplemented with 15 mg/i kanamycin. Incubation was carried out for 2 days at 33° C.

Plasmid DNA was isolated from a transformant by conventional methods (Peters-Wendisch et al., 1998, Microbiology, 144, 915–927), cleaved with the restriction endonuclease EcoRI, and the plasmid was checked by subsequent agarose gel electrophoresis. The resulting strain was called DSM5715/pJC1acp.

This microorganism was deposited at the Deutsche Sammlung fuir Mikrorganismen [sic] und Zelikulturen (DSMZ= German Collection of Microorganisms and Cell Cultures, Braunschweig, Germany) in accordance with the Budapest Treaty:

*Corynebacterium glutamicum*/pJC1acp as DSM 13247

Example 6

Preparation of Lysine

The *C. glutamicum* strain DSM5715/pJC1acp obtained in example 5 was cultured in a nutrient medium suitable for the production of lysine and the lysine content in the culture supernatant was determined.

For this, the strain was first incubated on an agar plate with the corresponding antibiotic (brain-heart agar with kanamycin (50 mg/l)) for 24 hours at 33° C. Starting from this agar plate culture, a preculture was seeded (10 ml medium in a 100 ml conical flask). The complete medium CgIII was used as the medium for the preculture.

Medium Cg III

| | |
|---|---|
| NaCl | 2.5 g/l |
| Bacto-Peptone | 10 g/l |
| Bacto-Yeast extract | 10 g/l |
| Glucose (autoclaved separately) | 2% (w/v) |

The pH was brought to pH 7.4

Kanamycin (25 mg/l) was added to this medium. The preculture was incubated for 24 hours at 33° C. at 240 rpm on a shaking machine. A main culture was seeded from this preculture such that the initial OD (660 nm) of the main culture was 0.1. Medium MM was used for the main culture.

Medium MM

| | |
|---|---|
| CSL (corn steep liquor) | 5 g/l |
| MOPS (morpholinopropanesulfonic acid) | 20 g/l |
| Glucose (autoclaved separately) | 50 g/l |
| $(NH_4)_2SO_4$ | |
| $KH_2PO_4$ | 25 g/l |
| $MgSO_4 * 7 H_2O$ | 0.1 g/l |
| $CaCl_2 * 2 H_2O$ | 1.0 g/l |
| $FeSO_4 * 7 H_2O$ | 10 mg/l |
| $MnSO_4 * H_2O$ | 10 mg/l |
| Biotin (sterile-filtered) | 0.3 mg/l |
| Thiamine * HCl (sterile-filtered) | 0.2 mg/l |
| L-Leucine (sterile-filtered) | 0.1 g/l |
| $CaCO_3$ | 25 g/l |

The CSL, MOPS and the salt solution were brought to pH 7 with aqueous ammonia and autoclaved. The sterile substrate and vitamin solutions were then added, as well as the $CaCO_3$ autoclaved in the dry state.

Culturing is carried out in a 10 ml volume in a 100 ml conical flask with baffles. Kanamycin (25 mg/l) was added. Culturing was carried out at 33° C. and 80% atmospheric humidity.

After 48 hours, the OD was determined at a measurement wavelength of 660 nm with a Biomek 1000 (Beckmann Instruments GmbH, Munich). The amount of lysine formed was determined with an amino acid analyzer from Eppendorf-BioTronik (Hamburg, Germany) by ion exchange chromatography and post-column derivatization with ninhydrin detection.

The result of the experiment is shown in table 1.

TABLE 1

| Strain | OD (660) | Lysine HCl g/l |
|---|---|---|
| DSM5715/pJC1acp | 12.67 | 14.63 |
| DSM5715 | 12.80 | 14.08 |

Example 7

Improvement in Growth Properties

The plasmid pJC1acp obtained in example 4 was used for transformation of *C. glutamicum* strain ATCC 13032. This strain was transformed as described in example 5 and checked by restriction digestion and agarose gel electrophoresis as described in example 5. The resulting strain ATCC 13032/pJC1acp was cultured in a nutrient medium suitable for determination of the growth and the growth was determined at various temperatures.

For this, the strain was first incubated, as described in example 6, on an agar plate with the corresponding antibiotic (brain-heart agar with kanamycin (50 mg/l)) for 24 hours at 30° C. Starting from this agar plate culture, a preculture was seeded (10 ml medium in a 100 ml conical flask). The complete medium CgIII described in example 6 was used as the medium for the preculture. Kanamycin (25 mg/l) was added to this. The preculture was incubated for 16 hours at 30° C. at 240 rpm on a shaking machine. A main culture was seeded from this preculture such that the initial OD (600 nm) of the main culture was 0.7. Medium MM was used for the main culture.

Medium MM

| | |
|---|---|
| MOPS (morpholinopropanesulfonic acid) | 42 g/l |
| Glucose (autoclaved separately) | 40 g/l |
| $(NH_4)_2SO_4$ | 20 g/l |
| $KH_2PO_4$ | 1.0 g/l |
| $K_2HPO_4$ | 1.0 g/l |
| $MgSO_4 * 7 H_2O$ | 0.25 g/l |
| $CaCl_2 * 2 H_2O$ | 10 mg/l |
| $FeSO_4 * 7 H_2O$ | 10 mg/l |
| $MnSO_4 * H_2O$ | 10 mg/l |
| $ZnSO_4 * H_2O$ | 1 mg/l |
| $CuSO_4$ | 0.2 mg/l |
| $NiCl_2 * 6 H_2O$ | 0.02 mg/l |
| Biotin (sterile-filtered) | 0.2 mg/l |
| Protocatechuic acid (sterile-filtered) | 30 mg/l |

MOPS and the salt solution were brought to pH 7 with aqueous ammonia and autoclaved. The sterile substrate and vitamin solutions were then added.

Culturing was carried out in a 60 ml volume in a 500 ml conical flask with baffles. Kanamycin (25 mg/l) was added.

Figure 2:
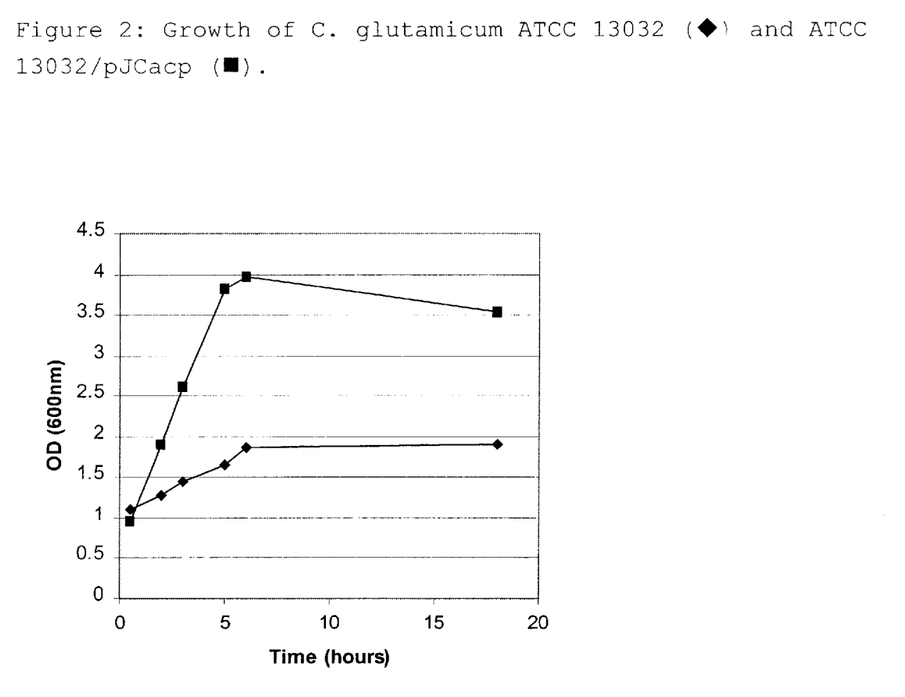
FIG. 2: Growth of *C. glutamicum* ATCC 13032 and ATCC 13032/pJCacp at 40° C.

Culturing was carried out at 40° C. The OD was determined at a measurement wavelength of 600 nm with the Ultrospec 3000 (Pharmacia Biotech, Upsala, Sweden). The result of the experiment is shown in FIG. 2.

Figure 1:
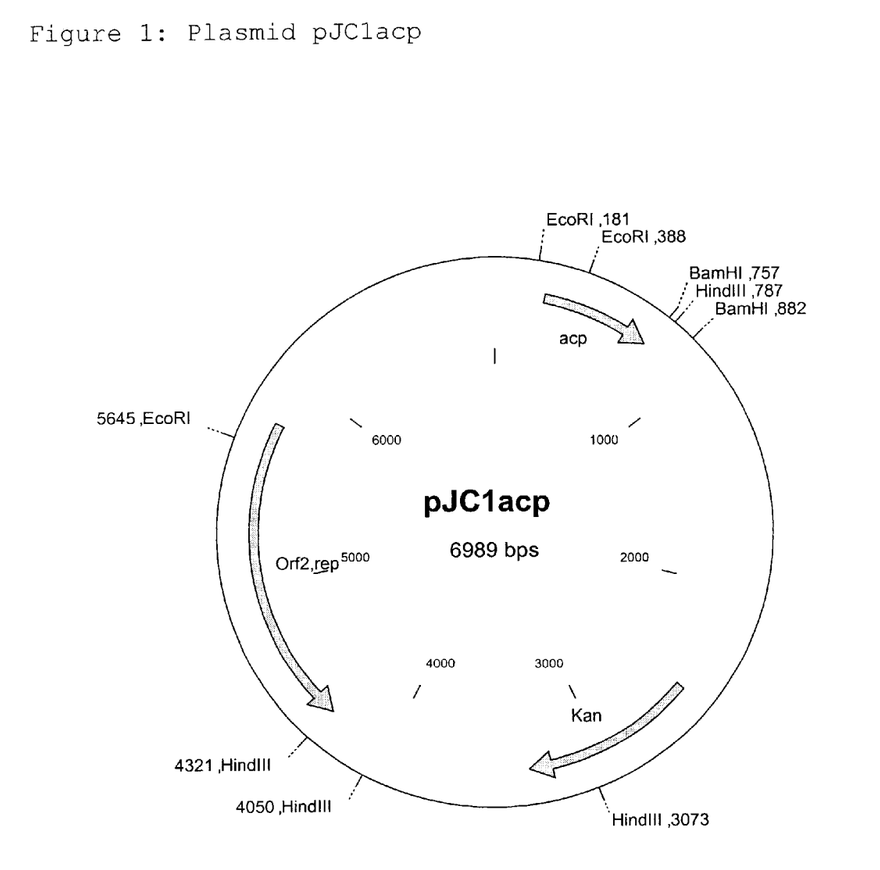
FIG. 1: Plasmid pJC1acp

The abbreviations used in the figures have the following meaning:

ori Cg Plasmid-coded replication origin from *C. glutamicum* (of pHM1519)

Kan: Resistance gene for kanamycin from pHM1519

Amp: Resistance gene for ampicillin acp: Acyl carrier protein of *C. glutamicum*

OD: Optical density

BamHI: Cleavage site of the restriction enzyme BamHI

EcoRI: Cleavage site of the restriction enzyme EcoRI

HindIII: Cleavage site of the restriction enzyme HindIII

What is claimed is:

1. An isolated polynucleotide consisting of a nucleotide sequence encoding a protein with an antic acid sequence comprising that of SEQ ID NO:2, wherein said protein has acyl carrier protein activity.

2. An isolated polynucleotide comprising the nucleotide sequence of nucleotides 58–348 of SEQ ID NO:1, wherein said polynucleotide encodes a polypeptide having acyl carrier protein activity.

3. An isolated polynucleotide comprising the nucleotide sequence of SEQ ID NO:1, wherein said polynucleotide encodes a polypeptide having acyl carrier protein activity.

4. A vector comprising the polynucleotide of any one of claims 1, 2 and 3.

5. The vector of claim 4, wherein said vector is a plasmid.

6. A bacterial host cell transformed with the vector of claim 5.

7. The bacterial host cell of claim 6, wherein said bacterial host cell is of the species *Corynebacterium glutamicum*.

* * * * *

UNITED STATES PATENT AND TRADEMARK OFFICE
CERTIFICATE OF CORRECTION

| | |
|---|---|
| PATENT NO. | : 6,830,921 B2 |
| APPLICATION NO. | : 09/852137 |
| DATED | : December 14, 2004 |
| INVENTOR(S) | : Möckel et al. |

It is certified that error appears in the above-identified patent and that said Letters Patent is hereby corrected as shown below:

On the Title Page of the patent:

Item (73) Assignee: "Degussa AG, Dusseldorf (DE)" should read --Degussa AG, Dusseldorf (DE) and Forschungszentrum Jülich GmbH, Julich (DE)--.

Signed and Sealed this

Twenty-second Day of May, 2007

JON W. DUDAS
*Director of the United States Patent and Trademark Office*